US00PP35365P2

(12) United States Plant Patent
Hancock

(10) Patent No.: US PP35,365 P2
(45) Date of Patent: Sep. 5, 2023

(54) BLUEBERRY PLANT NAMED 'MSU 120'

(50) Latin Name: *Vaccinium corymbosum*
Varietal Denomination: MSU 120

(71) Applicant: BOARD OF TRUSTEES OF MICHIGAN STATE UNIVERSITY, East Lansing, MI (US)

(72) Inventor: James F. Hancock, Scarborough, ME (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 17/803,700

(22) Filed: Oct. 17, 2022

(51) Int. Cl.
*A01H 5/08* (2018.01)
*A01H 6/36* (2018.01)

(52) U.S. Cl.
USPC ..... Plt./157
CPC ..... *A01H 6/368* (2018.05)

(58) Field of Classification Search
USPC ..... Plt./157
CPC ..... A01H 6/368; A01H 5/08
See application file for complete search history.

(56) References Cited

U.S. PATENT DOCUMENTS

| | | | |
|---|---|---|---|
| PP15,103 | P3 | 8/2004 | Hancock |
| PP15,146 | P3 | 9/2004 | Hancock |
| PP19,990 | P3 | 5/2009 | Ballington et al. |
| PP25,995 | P3 | 10/2015 | Hancock |
| PP32,110 | P2 | 8/2020 | Hancock |

*Primary Examiner* — Keith O. Robinson
(74) *Attorney, Agent, or Firm* — McKee, Voorhees & Sease PLC

(57) ABSTRACT

'MSU 120' is a new blueberry variety of *Vaccinium corymbosum*. 'MSU 120' is primarily *Vaccinium corymbosum* but is a complex hybrid with about 7.7% of its genes coming from *V. darrowii*, 6% from *V. angustifolium*, 1.7% from *V. virgatum*, and 0.2% from *V. tenellum*. It is a highly productive cultivar-with excellent fresh fruit quality. It is well adapted to all northern highbush production areas. Plants of 'MSU 120' are vigorous and upright, with numerous, moderately branched canes and well exposed fruit. Its berries are large, have small, dry picking scars, medium blue color, good firmness and flavor.

6 Drawing Sheets

Latin name and variety denomination: The present invention relates to a new and distinct variety of *Vaccinium corymbosum*, which is hereby denominated 'MSU 120'.

SUMMARY

This invention relates to a new and distinct variety of highbush blueberry plant. It has as its maternal parent 'New Hanover' and its paternal parent is 'Draper'. 'MSU 120' is primarily *Vaccinium corymbosum*, but is a complex hybrid with about 7.7% of its genes coming from *V. darrowii,* 6% from *V. angustifolium,* 1.7% from *V. virgatum*, and 0.2% from *V. tenellum*. It is a highly productive cultivar with excellent fresh fruit quality. It is likely well adapted to all northern highbush production areas. Plants of 'MSU 120' are vigorous and upright, with numerous, moderately branched canes and well exposed fruit. Its berries are large, have small, dry picking scars, medium blue color, good firmness and flavor.

The fruiting season of 'MSU 120' likely falls after 'Draper' and 'Katandin' but before 'Calypso' and 'Liberty'. 'MSU 120' has larger fruit than paternal parent 'Draper' with comparable firmness. It is a much more vigorous, upright plant than 'Draper' with more productive fruit yield. The internode length of 'MSU 120' is shorter than maternal parent 'New Hanover', but longer than 'Katandin', 'Calypso', or 'Liberty'. In addition, 'MSU 120' has shorter flowers, shorter pedicels, and fewer flowers per inflorescence than 'New Hanover', 'Katandin', 'Calypso', or 'Liberty'.

BRIEF DESCRIPTION OF PHOTOGRAPHS

The accompanying photographs display fruits, bunches, and leaves from a six-year-old mature blueberry plant in 2022.

DETAILED BOTANICAL DESCRIPTION

Figure 1:
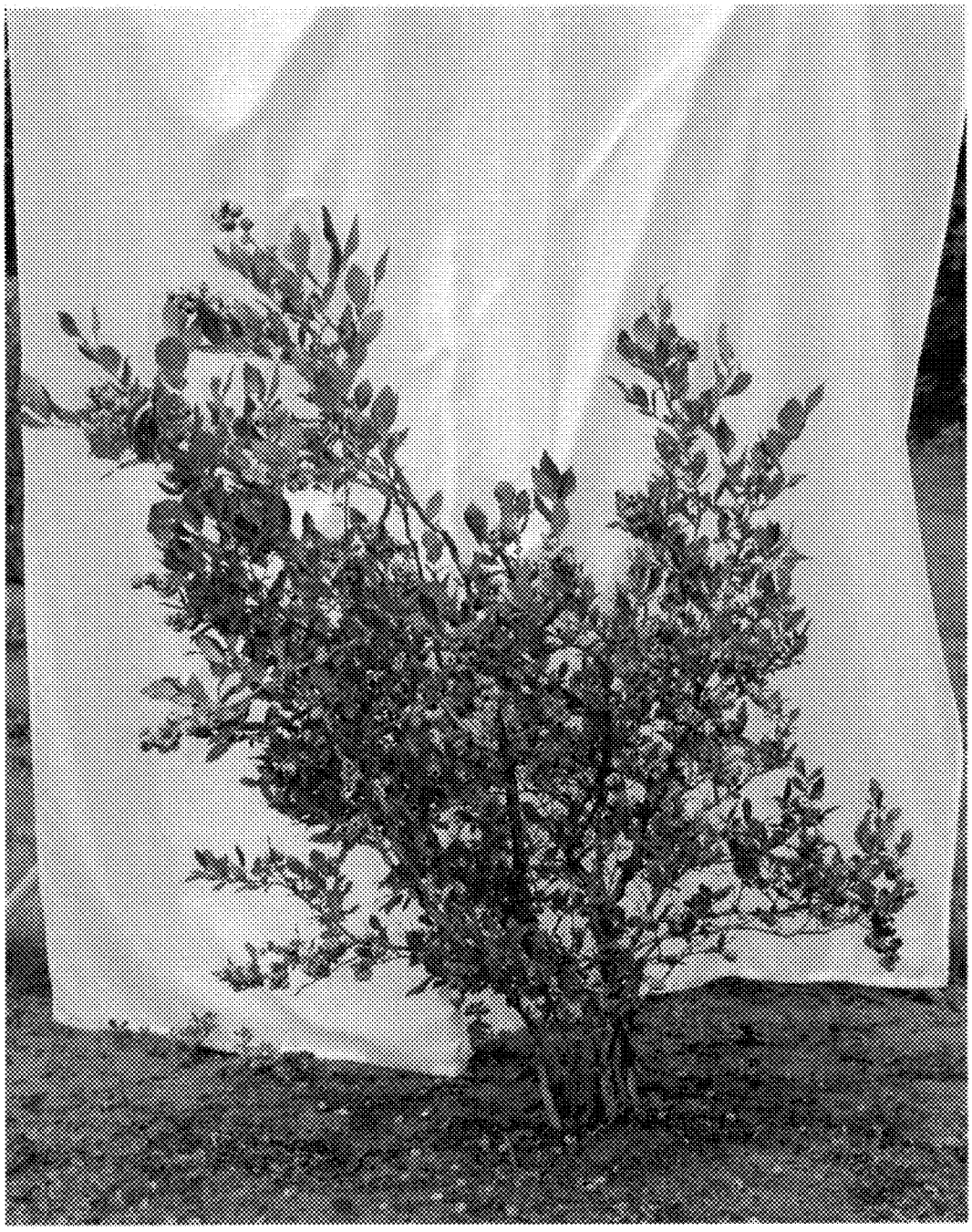
FIG. 1 is a photograph of the plant habit of 'MSU 120'.
Figure 2:
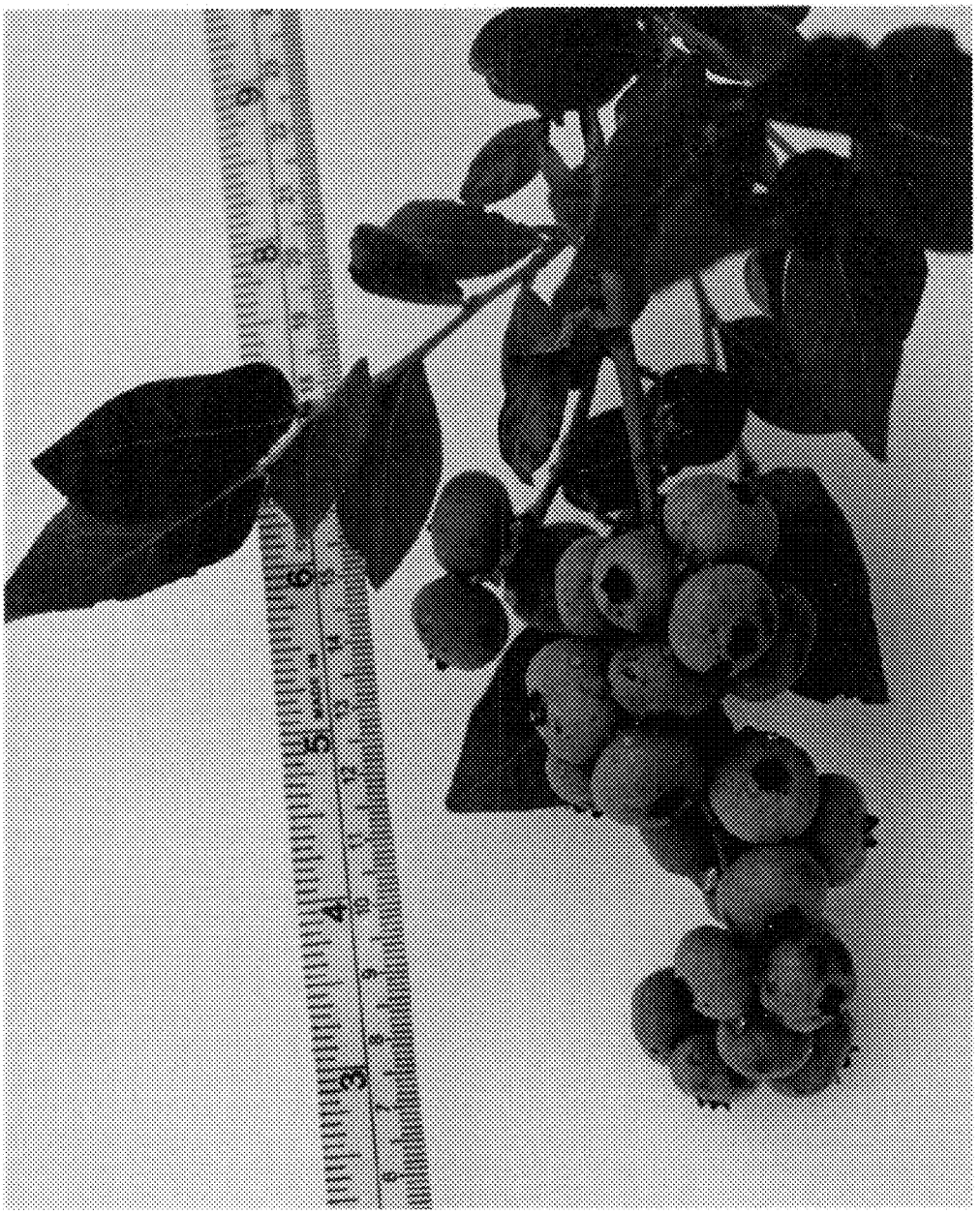
FIG. 2 is a photograph of a fruit bunch with foliage of 'MSU 120'.
Figure 3:
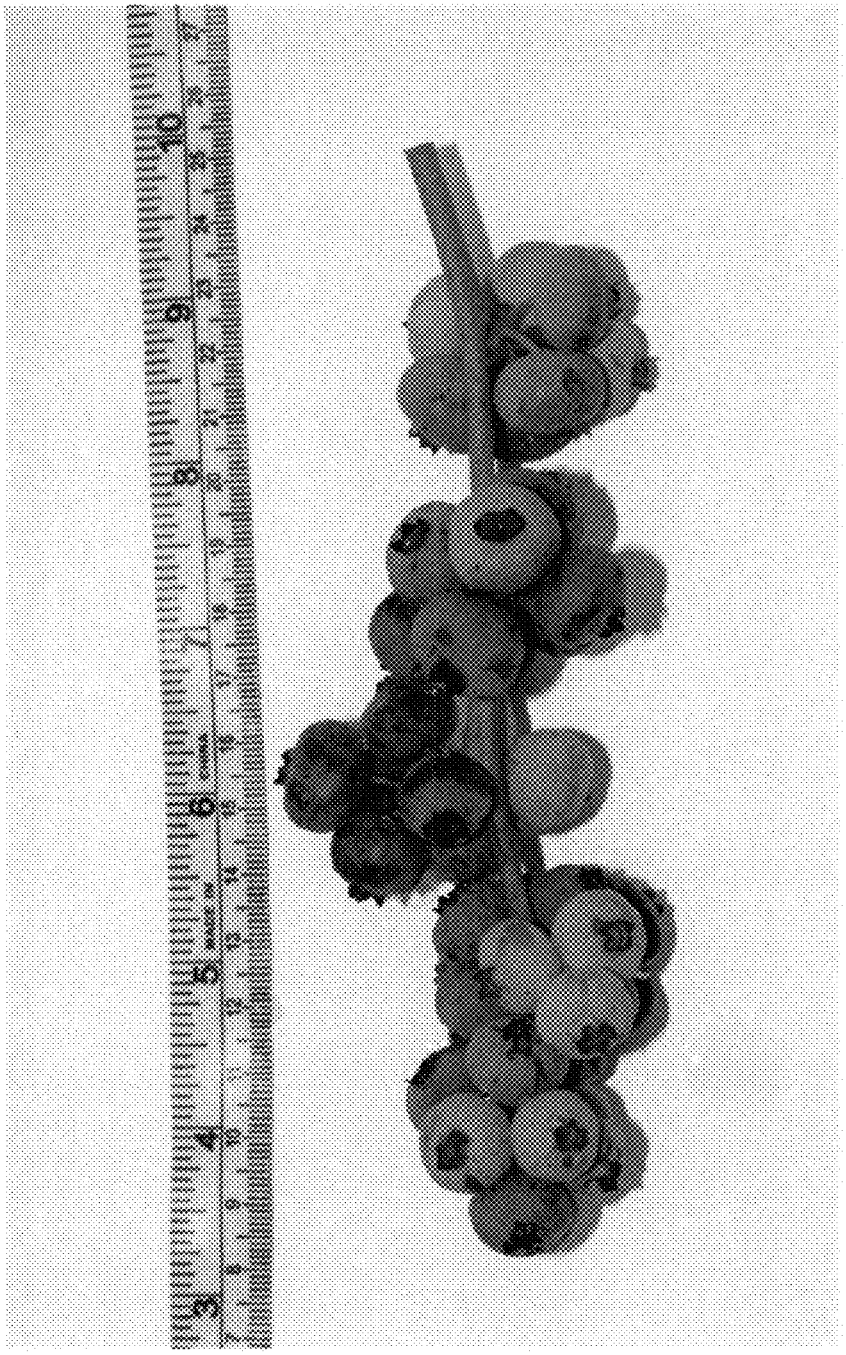
FIG. 3 is a photograph of a fruit bunch with foliage removed of 'MSU 120'.
Figure 4:
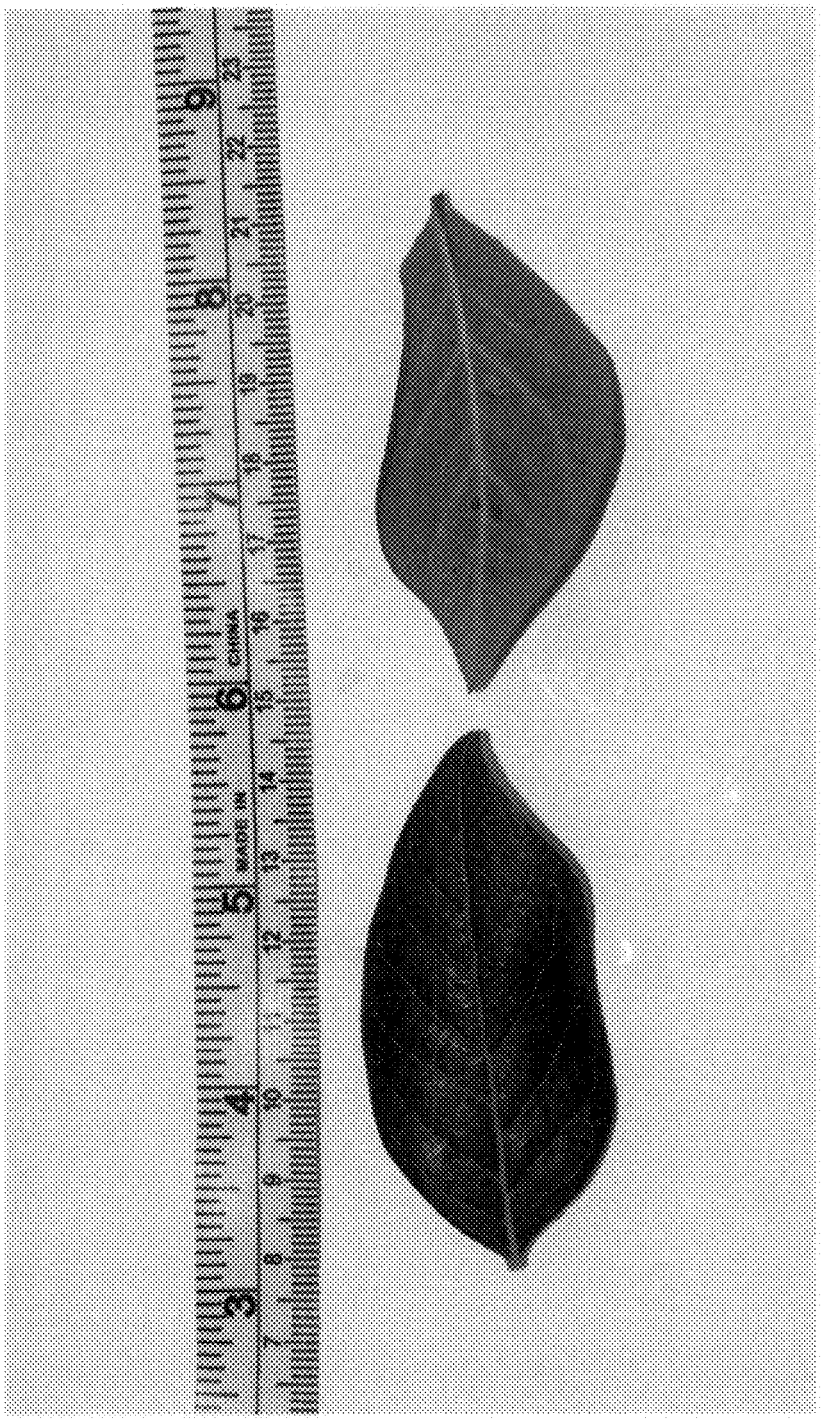
FIG. 4 is a photograph of the leaves of 'MSU 120'. (Left) upper surface of leaf (Right) lower surface of leaf.
Figure 5:
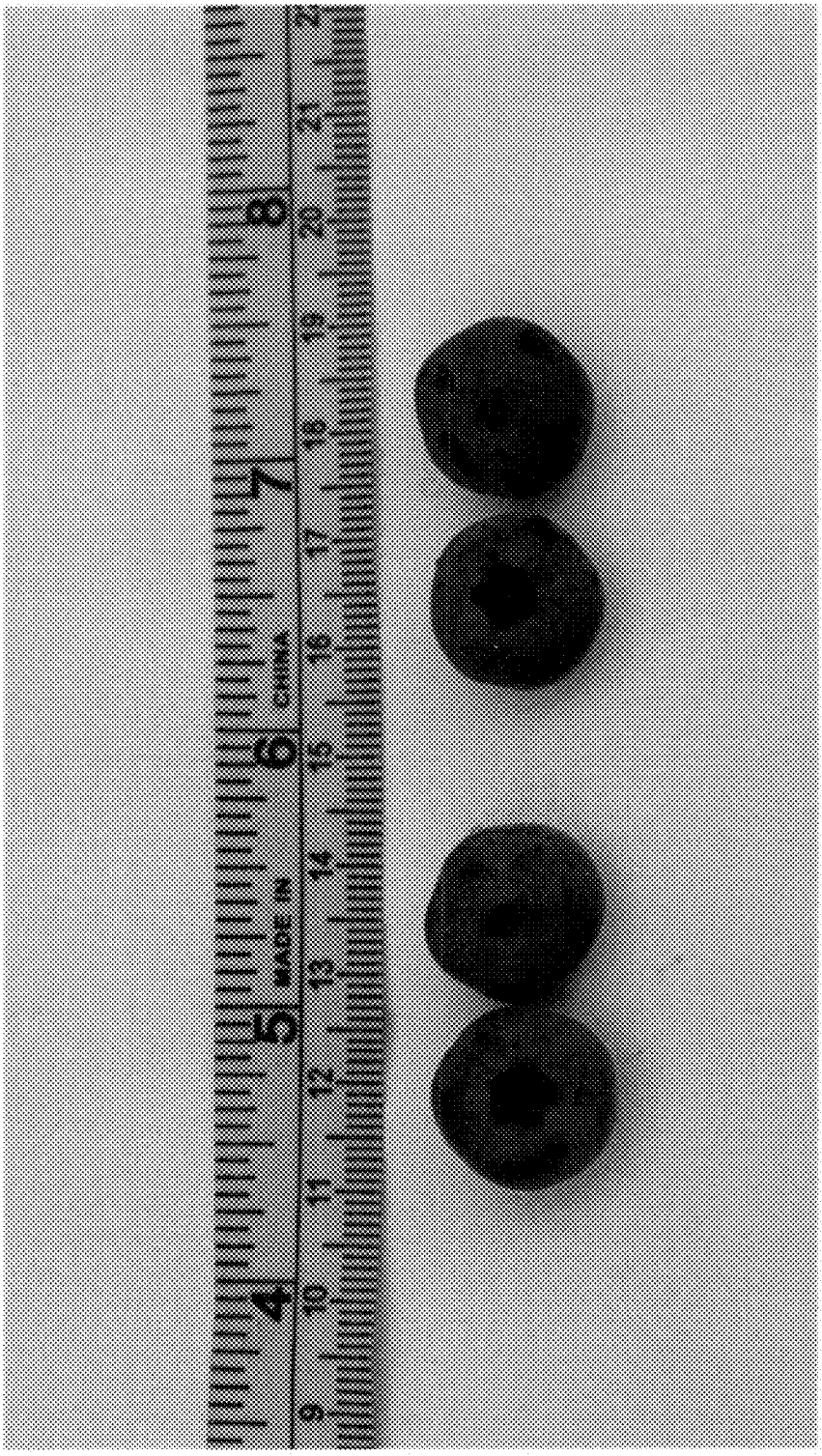
FIG. 5 is a photograph of fruit of 'MSU 120'.
Figure 6:
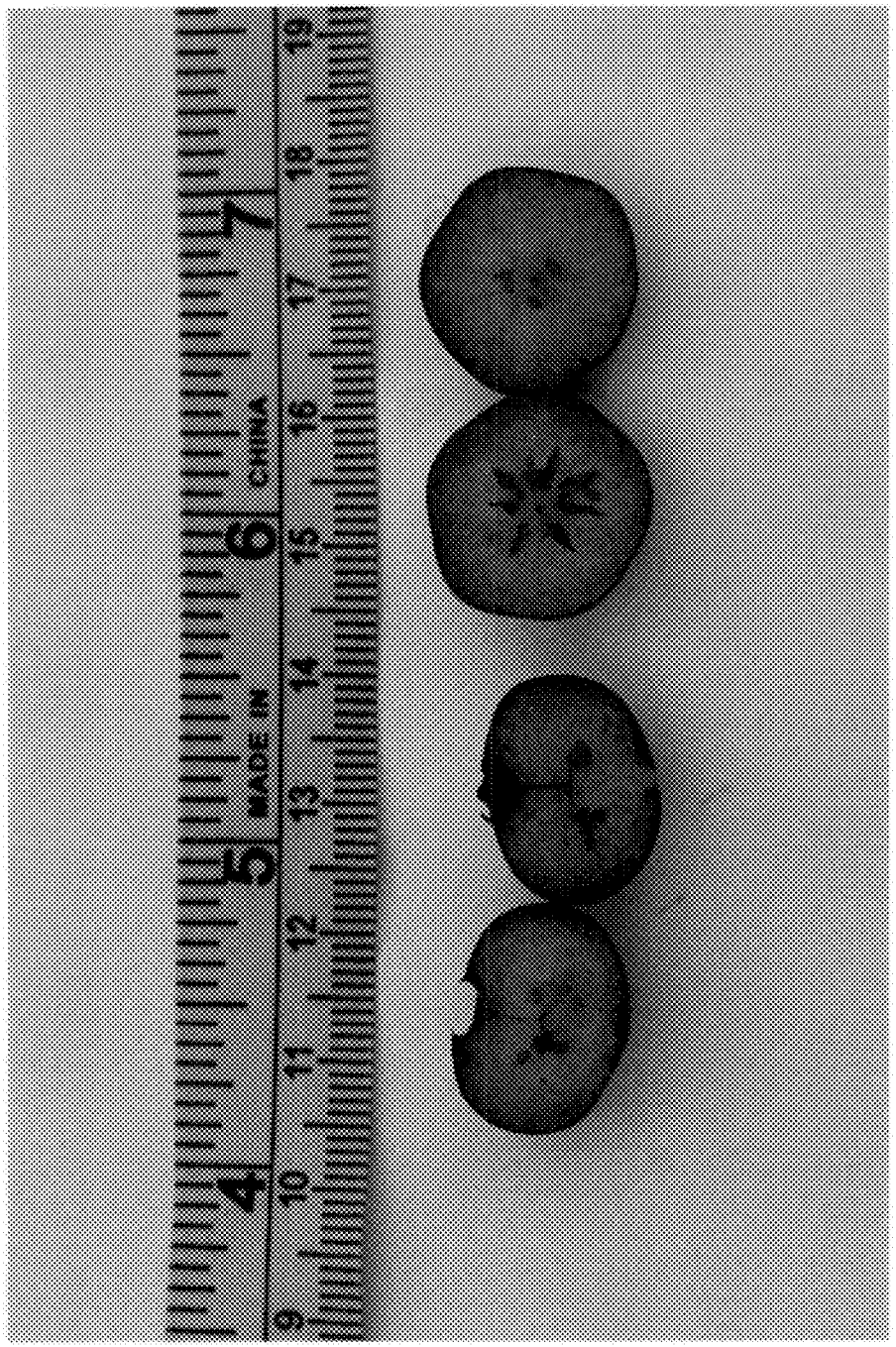
FIG. 6 is a photograph of cut fruit of 'MSU 120'.

The following is a detailed botanical description of the new and distinct variety of blueberry denominated 'MSU 120', its flowers, fruit, and foliage, as based on observations of a six-year-old plant. The taxonomic characteristics chosen in the detailed description are standard in the practice (R E Gough, R J Hindle, and V G Shutak, "Identification of Ten Highbush Blueberry Cultivars using Morphological Characteristics," HortScience 11 (5): 5124, 1976). Color descriptions, except those given in common terms, are presented in Royal Horticultural Society Colour Chart (1995 Edition) designations. In cases where the color descriptions cited from The Royal Horticultural Society Colour Chart differ from the colors shown in the drawings, the colors cited from The Royal Horticultural Society Colour Chart should be considered accurate. Any deviation from these colors in the drawings is due to failure of the photographic process to exactly duplicate the colors of nature. In addition, fruit color designations in Table 1 are applicable only to mature fruit.

TABLE 1

| 'MSU 120' characteristics |
|---|
| Plant traits |
| Mature height - 1.16 m |
| Mature width - 1.01 m |
| Height/width ratio - 1.16 |
| Growth habit - upright |
| Vigor - strong |
| Annual renewal canes - 2 to 4 |
| Internode length on spring shoots - 4.05 cm |
| Mature cane color - gray brown (199D) |
| Mature cane length - 1.07 |
| Mature cane width - 3.7 cm |
| Bark texture - rough and flakey |
| New shoot color (one-year-old) - greyed green (197A) |
| Fruiting type - one-year-old shoots only |
| Fruit bloom intensity - strong |
| Density of infructescence - sparse |
| Beginning of vegetative growth - medium |
| Beginning of flowering (one-year-old shoots) - medium |
| Beginning of fruit ripening (one-year-old shoots) - medium |
| Foliage |
| Leaf shape - ovate |
| Apex shape - acute |
| Base shape - acute |
| Leaf length - 6.93 cm |
| Leaf width - 3.9 cm |
| Leaf length/width ratio - 1.8 |
| Leaf margin - entire |
| Leaf nectaries - absent |
| Pubescence - none |
| Color upper surface - dark green (138B) |
| Color lower surface - yellowish green (142C) |
| Petiole length - 1.7 cm |
| Petiole color - yellowish green (142C) |
| Bud |
| Bud shape - ovate |
| Bud width - 3.8 mm |
| Bud length - 5.5 mm |
| Color - reddish brown |
| Blossoms |
| Shape of corolla - urceolate |
| Calyx - five-lobed |
| Style length - 5.9 mm |
| Color of open flower - white |
| Flower # per cluster - 6 |
| Pistil - even with corolla |
| Pistil color - yellowish green (146C) |
| Pistil length - 6.19 mm |
| Flower diameter - 6.53 mm |
| Flower length - 6.67 mm |
| Fragrance - faint blueberry aroma |
| Calyx diameter - 3.96 mm |
| Sepals |
| Length - 2.02 mm |
| Width - 2.66 mm |
| Sepal Color top - yellowish green (146C) |
| Sepal Color bottom - yellowish green (146C) |

TABLE 1-continued

| 'MSU 120' characteristics |
|---|
| Reproductive organs |
| Type berry |
| Seed size - 1.32 mm |
| Number of seeds - 12.7 |
| Mature fruit |
| Height - 1.35 cm |
| Width - 1.76 cm |
| Color with bloom - light blue (98D) |
| Color without bloom - black (103 A) |
| Pedicel scar size - 1.08 |
| Pedicel length - 0.84 cm |
| Pedicel color - yellowish green (146C) |
| Peduncle length - 12 mm |
| Peduncle color - yellowish green (146C) |
| Average weight - 2.4 gm |

Emasculated flowers of 'New Hanover' (U.S. Plant Pat. No. 19,990) were pollinated in 2008 with pollen from 'Draper' (U.S. Plant Pat. No. 15,103). The seeds were germinated, grown in a greenhouse for 1 year and then field planted in Benton Harbor, Mich. 'MSU 120' was first selected from a group of 52 siblings in 2011.

The original selection of 'MSU 120' was evaluated in Benton Harbor, Mich. from 2009-2013. Rooted cuttings were also set in advanced trials at Grand Junction, Mich., Silverton, Oreg., Lowell, Oreg., and Virquenco, Chile. Two-year-old plants were set at 4'×10' spacing in Michigan in 2014 and the other locations in 2015. The plantings in Chile and Oregon were evaluated for two years, and the one in Michigan for six years.

'MSU 120' may be propagated by hardwood cuttings in a greenhouse and then planted in the field. Initiation of root development from hardwood cuttings may take about four to six weeks.

Initiation of root development from microshoots takes about three to four weeks. Such methods are discussed in the following references, incorporated by reference herein: Doran, W. L. and Bailey, J. S. "Propagation of the high bush blueberry by softwood cuttings," Bulletin Massachusetts Agricultural Experiment Station; no. 410. Amherst, Mass. Massachusetts State College, 1943; Doehlert, C. A. "Propagating blueberries from hardwood cuttings," Circular (New Jersey Agricultural Experiment Station) 490. New Brunswick, N.J. New Jersey Agricultural Experiment Station, 1945; Doehlert, C. A. "Propagating blueberries from hardwood cuttings," Circular (New Jersey Agricultural Experiment Station) 551. New Brunswick, N.J.: New Jersey Agricultural Experiment Station, 1953; Zimmerman, R. H. 1991. Micropropagation of temperate zone fruit and nut crops. In: Debergh, P. C. and Zimmerman, R. H. (eds.) Micropropagation: Technology and application. Kluwer, Dordreckt; El Shiekh, A.; Wildung, D. K.; Luby, J. J.; Sargent, K. L.; Read, P. E. "Long term effects of propagation by tissue culture or softwood single node cuttings on growth habit, yield, and berry weight of 'Northblue' blueberry," Journal of the American Society for Horticultural Science. 1996, 121: 2, 339 342; Galletta, G. J.; Ballington, J. R.; Daubeny, H. A.; Brennan, R. M.; Reisch, B. J.; Pratt, C.; Ferguson, A. R.; Seal, A. G.; McNeilage, M. A.; Fraser, L. G.; Harvey, C. F.; Beatson, R. A.; Hancock, J. F.; Scott, D. H.; Lawrence, F. J.; Janick, J. (ed.); Moore, J. N. "Fruit breeding. Volume II. Vine and small fruits," Department of Horticulture, Purdue University, West Lafayette, Ind. 1996 John Wiley and Sons;

New York; USA; Strik, B.; Brun, C.; Ahmedullah, M.; Antonelli, A.; Askham, L.; Barney, D.; Bristow, P.; Fisher, G.; Hart, J.; Havens, D. Draper A. D. and Chandler C. K. "Accelerating highbush blueberry selection evaluation by early propagation," Journal of the American Society for Horticultural Science. 1986 111(2): 301-303; Pritts M. P. and Hancock J. F. (Eds.) "Highbush blueberry production guide," Northeast Regional Agricultural Engineering Service, Ithaca, N.Y., USA 1992.

Asexual propagation as described has demonstrated that the combination of traits that characterize this blueberry are fixed and remain true to type through at least two successive propagation cycles.

'MSU 120' is primarily *Vaccinium corymbosum*, but is a complex hybrid with 7.7% of its genes coming from *V. darrowii,* 6% from *V. angustifolium,* 1.7% from *V. virgatum*, and 0.2% *V. tenellum*. It is a highly productive cultivar with excellent fresh fruit quality. It is likely well adapted to all northern highbush production areas. Plants of 'MSU 120' are vigorous and upright, with numerous, moderately branched canes and well exposed fruit. Its berries are large, have small, dry picking scars, medium blue color, good firmness and flavor. The fruiting season of 'MSU 120' likely falls after 'Draper' and 'Katandin' (U.S. Plant Pat. No. 32,110), but before 'Calypso' (U.S. Plant Pat. No. 25, 995) and 'Liberty' (U.S. Plant Pat. No. 15,146).

Table 2 presents development and fruit characteristics of 'MSU 120' as grown in four locations. Evaluations were made when the bushes were 30-50% ripe. For bush habit, 1=sprawling, 5=bushy and 9=upright. For season, 1=very early, 4-5=mid-season and 9=very late. The rating scale for fruit characteristics was 1-9, with 1-4=inferior, 5-6=acceptable, 7=good, 8=excellent and 9=superior.

TABLE 2

| | | | | | Fruit Characteristics | |
|---|---|---|---|---|---|---|
| Location | | Year | Habit | Season | Yield | Size |
| Michigan | Grand Junction | 2016 | 8 | 3 | 10 | 8 |
| | | 2017 | 8 | 4 | 8 | 8 |
| | | 2018 | 7 | 5 | 6 | 8 |
| | | 2019 | 8 | 4 | 9 | 8 |
| Chile | Virquenco | 2018 | 8 | 4 | 9.5 | 8 |
| | | 2019 | 8 | 4 | 8 | 8 |
| Oregon | Lowell | 2017 | 7 | 4 | 8 | 7 |
| | | 2020 | 4 | 7 | 8 | 8 |
| | Silverton | 2016 | 8 | 3.5 | 5 | 8 |
| | | 2017 | 8 | 4 | 5 | 7 |
| | Mean | | 7.4 | 4.3 | 7.7 | 7.8 |

| | | | Fruit Characteristics | | | |
|---|---|---|---|---|---|---|
| Location | | Year | Color | Scar | Firmness | Flavor |
| Michigan | Grand Junction | 2016 | 8 | 8 | 8 | 7 |
| | | 2017 | 7 | 9 | 8 | 7 |
| | | 2018 | 7 | 8 | 8 | 8 |
| | | 2019 | 8 | 9 | 9 | 6 |
| Chile | Virquenco | 2018 | 8 | 9 | 8 | 7 |
| | | 2019 | 7 | 8 | 8 | 8 |
| Oregon | Lowell | 2017 | 7 | 8 | 7 | |
| | | 2020 | 4 | 3 | 4 | |
| | Silverton | 2016 | 5 | 8 | 5 | |
| | | 2017 | 5 | 8 | 4 | |
| | Mean | | 6.6 | 8.2 | 6.9 | 7.2 |

In multi-location trials, 'MSU 120' has proven to be an extremely upright very vigorous bush that ripens in the mid-season, as presented in Table 2. At most locations, it has produced good to excellent yields and its fruit have had good to excellent size, color, firmness and flavor, although at Silverton Oreg., 'MSU 120's' yields and color were reported to be just acceptable.

Table 3 presents mean fruit ratings and ranges (in parentheses) of 'MSU 120' and 2 other cultivars as grown and observed in Grand Junction, Mich. in 2016, 2017, and 2018. Two-year-old plants were set in 2014. Fruit evaluations were made when the bushes were 30-50% ripe. The rating scale for the vigor, hardiness and fruit characteristics were 1-9, with 1-4=inferior, 5-6=acceptable, 7=good, 8=excellent and 9=superior. For bush habit, 1=sprawling, 5=bushy and 9=upright.

TABLE 3

| Cultivar | Date First Harvest | Plant Habit | Winter Hardiness | Plant Vigor | Fruit Weight |
|---|---|---|---|---|---|
| 'Bluecrop' | 7/4 (7/2-7/6) | 5.7 (5-6) | 7.5 (6-8) | 6.9 (6-7) | 6.5 (6-7) |
| 'Draper' | 7/4 (6/24-7/7) | 6.7 (6-7) | 8 (7-9) | 5.5 (5-6) | 7.6 (7-9) |
| 'MSU 120' | 7/12 (7/9-7/14) | 7.7 (7-8) | 7.5 (6-8) | 7 (7) | 8 (8) |

| Cultivar | Fruit Color | Picking Scar | Firmness | Flavor | Yield |
|---|---|---|---|---|---|
| 'Bluecrop' | 6.5 (6-7) | 7.5 (7-8) | 8.0 (7-9) | 6.5 (6-7) | 5.5 (5-6) |
| 'Draper' | 8.5 (8-9) | 8.6 (8-9) | 8.8 (8-9) | 7.2 (7-8) | 6.5 (5-9) |
| 'MSU 120' | 7.5 (7-8) | 8.5 (8-9) | 8.7 (8-9) | 7.0 (6-8) | 7.7 (7-8) |

'MSU 120' has ripened an average of 8 days after 'Draper' and 'Bluecrop' (not patented), as presented in Table 3. It has a more upright plant habit and higher yields than both 'Draper' and 'Bluecrop', with comparable fruit quality except it is a little darker. 'MSU 120' has been superior to 'Bluecrop' for fruit weight, color, firmness and scar.

Table 4 presents average fruit physical and biochemical characteristics of 'MSU 120' compared to other cultivars in Grand Junction, Mich. Three, five-fruit samples were evaluated when the bushes were 30-50% ripe. Means followed by the same letter in a column are not significantly different.

TABLE 4

| Cultivar | Year | Weight (g) | Soluble Solids | Titratable Acidity | SS/TA | Firmness (g/mm) |
|---|---|---|---|---|---|---|
| 'MSU 120' | 2019 | 2.3 ab | 12.1 b | 0.91 b | 13.2 ab | 269 a |
| | 2020 | 2.5 a | 12.7 ab | 1.01 c | 12.6 ab | 185 a |
| 'Bluecrop' | 2019 | 1.6 c | 14.6 a | 1.01 c | 14.4 b | 181 bc |
| | 2020 | 2.3 ab | 11.8 c | 0.67 a | 16.6 bc | 163 b |
| 'Calypso' | 2019 | 2.3 ab | 12.1 b | 0.73 a | 16.6 bc | 201 bc |
| | 2020 | 2.1 b | 13.3 a | 1.03 c | 12.9 ab | 173 ab |
| 'Draper' | 2019 | 2.1 b | 12.7 b | 0.89 ab | 14.3 b | 234 a |
| | 2020 | 2.3 ab | 11.7 c | 1.05 c | 11.3 a | 167 b |
| Katahdin' | 2019 | 2.1 b | 11.2 c | 0.91 b | 12.3 ab | 240 a |
| | 2020 | 2.5 a | 12.0 c | 1.11 c | 10.8 a | 165 b |
| 'Liberty' | 2019 | 2.0 c | 14.0 a | 0.76 a | 18.4 c | 177 c |
| | 2020 | 2.1 b | 13.6 a | 0.80 ab | 17.0 c | 186 a |

'MSU 120' was consistently among the largest fruited and firmest mid-season cultivars at Grand Junction, Mich. It generally ranked in the middle for soluble solids (SS) and titratable acidity (TA). The ratio of SS/TA in 'MSU 120' was not significantly different than 'Draper' and 'Katandin' in both 2019 and 2020, but was significantly lower than 'Liberty'.

Table 5 presents distinguishing characteristics for 'MSU 120' and comparative varieties 'New Hanover', 'Katandin', 'Calypso', and 'Liberty'. Compared to maternal parent 'New Hanover', 'MSU 120' has an earlier fruiting season, a shorter internode length, shorter flowers, shorter pedicels, and fewer flowers per inflorescence.

TABLE 5

| | MSU 120 | New Hanover | Katahdin | Calypso | Liberty |
|---|---|---|---|---|---|
| Fruiting season | Mid | Early-Mid | Early-Mid | Mid-Late | Late |
| Plant height | 1.15 m | 1.5 m | 1.4 m | 1.3 m | 1.5 m |
| Plant width | 1.0 m | 1.1 m | 1.1 m | 0.9 m | 1.2 m |
| Internode length on new growth | 41 mm | 130 mm | 15.6 mm | 17 mm | 25 mm |
| Leaf length | 69 mm | 54 mm | 50 mm | 50 mm | 37 mm |
| Leaf width | 18 mm | 33 mm | 24 mm | 24 mm | 20 mm |
| Petiole length | 1.7 mm | 3 mm | 1.7 mm | 1.7 mm | 4 mm |

TABLE 5-continued

| | MSU 120 | New Hanover | Katahdin | Calypso | Liberty |
|---|---|---|---|---|---|
| Leaf margin | entire | entire | entire | entire | serrated |
| Flowers per inflorescence | 6 | 7 | 8 | 6.5 | 9 |
| Flower length | 6.7 mm | 9 mm | 10.5 mm | 10.5 mm | 9.5 mm |
| Flower width | 6.5 mm | 6.8 mm | 8.5 mm | 6.5 mm | 6 mm |
| Fruit Length | 13.5 mm | 14 mm | 10 mm | 11 mm | 12 mm |
| Fruit width | 17.6 mm | 20 mm | 16 mm | 16 mm | 16 mm |
| Pedicel length | 0.8 mm | 5 mm | 7.5 mm | 7.5 mm | 2.5 mm |
| Fruit scar | 1.1 mm | 3 mm | 1.8 mm | 1.8 mm | 1.4 mm |

'MSU 120' is intended for all northern highbush production areas including Michigan, the easter US and Canada, central Chile, Europe, SE Asia, China, and the Pacific Northwest. It compares very favorably with the northern highbush cultivars now being grown for fruit weight and firmness.

What is claimed is:

1. A new and distinct highbush blueberry plant named 'MSU 120', substantially as described and illustrated herein.

* * * * *